ID US007329500B2" /># United States Patent
Martin et al.

(10) Patent No.: US 7,329,500 B2
(45) Date of Patent: Feb. 12, 2008

(54) MORAXELLA (BRANHAMELLA) CATARRHALIS POLYPEPTIDES AND CORRESPONDING DNA FRAGMENTS

(75) Inventors: Denis Martin, St-Augustin-de-Desmaures (CA); Josée Hamel, Sillery (CA); Bernard R. Brodeur, Sillery (CA); Stéphane Rioux, Beauport (CA); Julie Couture, St-Augustin-de-Desmaures (CA)

(73) Assignee: ID Biomedical Corporation, Laval (CA)

( * ) Notice: Subject to any disclaimer, the term of this patent is extended or adjusted under 35 U.S.C. 154(b) by 488 days.

(21) Appl. No.: 10/487,783

(22) PCT Filed: Aug. 27, 2002

(86) PCT No.: PCT/CA02/01315

§ 371 (c)(1),
(2), (4) Date: Feb. 26, 2004

(87) PCT Pub. No.: WO03/018052

PCT Pub. Date: Mar. 6, 2003

(65) Prior Publication Data

US 2004/0242859 A1    Dec. 2, 2004

(51) Int. Cl.
*G01N 33/53*    (2006.01)

(52) U.S. Cl. .................. 435/7.1; 530/300; 530/350; 424/184.1; 424/185.1; 424/190.1; 424/192.1; 424/193.1; 424/194.1; 424/251.1; 435/975; 435/7.32

(58) Field of Classification Search ............ 530/300, 530/350; 424/184.1, 185.1, 190.1, 192.1, 424/193.1, 194.1, 251.1; 435/975, 7.1, 7.32
See application file for complete search history.

(56) References Cited

U.S. PATENT DOCUMENTS 6,673,910 B1 *   1/2004   Breton ............... 536/23.1

FOREIGN PATENT DOCUMENTS

| WO | WO 00/09694 | 2/2000 |
|---|---|---|
| WO | WO 01/19996 | 3/2001 |

OTHER PUBLICATIONS

Murphy et al. Pediatr. Infect. Dis. J. 1989. 8: S66-S68.*
Yamanaka et al (J. Pediatrics. 1993. 122(2): 212-218).*
McMichael, "Progress Toward the Development of a Vaccine to Prevent *Moraxella (Branhamella) Catarrhalis* Infections," *Microbes and Infection* 2(5):561-568, Apr. 2000.

* cited by examiner

*Primary Examiner*—Jennifer E. Graser
(74) *Attorney, Agent, or Firm*—Seed IP Law Group PLLC

(57) ABSTRACT

The present invention relates to polypeptides of *Moraxella (Branhamela) catarrhalis* which may be used for prophylaxis, diagnostic and/or therapy purposes.

10 Claims, 2 Drawing Sheets

Figure 1

```
   1 ATGCACACCG CTCATCACCA TCGCTCAAAG ACATATTTGA CTACCGCTAT TCGTTACGCA
  61 CTATTTGGTA TCGCCAGTTT GCCATTTGTC ATACCAACTT ATGCAGAACT CAATACCAGC
 121 CGTTCACTGA CAGTCGTTGG TGCTGACAGC TCAAAAAATT TGCCTGATAC ACCAAATACC
 181 AAACCCAATA CTGTCTTAGC CTTAGACGCC CATCTACAAA GTCATGATGA TACTGCCAAT
 241 GCCTTTGATG GCTTTGATTT TGAAGTTATC ACACAGCAGG CAGCCGAGCA GACAAGCAGT
 301 CAAGCAAATC AAGGCAATCA TCAGATGAGC CAGCTTGACG CCTTTGCTAG TAAGTCAGAC
 361 AATCCAAGTT TAAACACTGC CAGGCTGACG GATAAGCATG ATACACCCTC TGCCAGTAAA
 421 AGCTTAGCCA AATTAGCCGA AAACTACCAT ATTAAGTCCG ATCCAGACGC TCATCGTTGT
 481 CAGGGTATGT GGATGCAGCC AATCCACCAA GCAACACACA CAAACCGCCC TACCACCCCA
 541 AAACTGGATG AAAATGGTAA TCCGATTACA GAAGATGGTA TTTTTGCTCA AGCTGATTAT
 601 GGATATTATG ACGCTCAAAC TTATGCCGAA CTGTCTGGCA ATGTCATTAT GGAACAAAAC
 661 GGTCGGCGTG TAACCGCTGA TAAGCTTACT TTAGACACCC AAACAGGGCA AGCCACTGCG
 721 TCAGGTCAAG TACAATTTAG TGATGGCGGT GCAAGTGATC ACAGTGCTGG CATTATTGGC
 781 ATGGCTGAAA ACTTAGTATA CCATACAGAT GGTCAGACAG CGACCGCACA AGATGTTGCT
 841 TTTGCAAGCA CTACCATCAA TGCTCACGGT TATGCCAGTC AAATGGATAA AATAAGCAGT
 901 AGCGAATATC GGCTTCAACA TGTCATGTTC ACCACCTGTC CACCCACAGA ACGCAAATGG
 961 TACTTAGATA CTGATAGCAT TGATATCAAT ACCGATACAG GTCGTGCTAT CGCCAAAAAT
1021 ACCACCTTGC GTATCAAAAA AGTACCTGTC TTTTACCTGC CCTATTTTAA CTTTCCGATC
1081 GATGCTCGTC GCTCTTCTGG ATTTTTATTA CCATCAATGG GATTGGTGC ATCGGACAGT
1141 TTTGAAATTA GTACGCCTTA TTATCTGAAT TTGGCACCAG ATTATGATGC AACCATTACG
1201 CCAACTGTAT TTACTAACCG CAATCCTATG CTGACTGGCG AATTTCGTTA TCTGACCCAA
1261 GATTATGGAT CAGGGGTGTT GACTGCTTCG TATCTTCCAA AAGATCAGCA ATATCATGAT
1321 AAAGACCGTA GCCGAATACA ATTTGATCAT ACATGGCAAC CCAAGCAGTT TGATAAAATT
1381 ACCACTTACG CACAATATCA ATCTGTTTCT GATGCCAATT ATTTATCAGA CTTTAATGCC
1441 TTGGGTGTTG AGAGTGCTAA GCTAAATCTA CCAAGACGCA TCGGCACAAG CTTCTTGGAT
1501 GAAAATGTCT CAGCTGATTT AAGATTTGAA GATTTTCAGC GTTTAGACGG TTTTGGCTTA
1561 GATGGTCGGC CAATTACAGA CAAAGATAGA CCATATGCAC GCCTACCACA GCTATCGGTC
1621 AACTATCGTT TGCCTCGCAT ATGGATGGGT ACACCCAGCG TCTTGAACT GGGTGGTATT
1681 CATAATTCTG CCTATTTCAA AAAATCCATT AAAGATAACT CTGAACCAGA AAAAAGCGGT
1741 GGTAGAATAT TTAACCAATT CACAGCCAGT TATCCACTGC TTCGCTCTTG GGGTTATTTG
1801 ACGCCAAAAC TTAGCCTGAC ACATCTATAT ACCAGCTATG ACGAAGACAG CTTAGCCGAC
1861 CAAAATATCG CTAAGAAAAA TGGTCGCCAT TCGGTATTTG CACCGACGGT CAGCTTGGAT
1921 GCTGGGCTAT TTTTTGAAAA AGCGGGTGCA CCATTTGGCA TGCATCAAGA TACAGGTGGC
1981 TATCAAGTAC TGACACCAAG ATTACACTAT ACTTACACGC CTTTTAAAGA TCAACACAAT
2041 GTACCAAATT TTGAGACAAA AATTGCACAG CTTAGCTATG AGCAGCTTTT GAACAATAAC
2101 TGGTTTTTGG GTCATGATCG CATTCAAGAT TTACACGCCG TCACGCCTGC AGTCAGCTAC
2161 CGTTATATAG ATAAAATGGG CAGGACACGC TTTGAAGGCG GATCGCAGA ACAGATTTTA
2221 TTGAGTCATA TCCGTGTTGG TATCAATGAC AGCGAAAGCT ATAGCAGCAG AAGCTCTGGT
2281 TTGGCATGGC AAGCCAGCCT ACAGCCAAAA GACAATTTAT GGTTTGATGC ATCAGGTTCA
2341 TTTAGAACAA ATTATGATTT GAGCAGTATT GTGGCACAAA TTCGCTATCG TCCAAGTGAT
2401 CGTAAGTTAT TTAACCTAGG TATTGTCAAA AGAAAGAAA ATCGTGCTTT TAATCAATCA
2461 GCATTATCAG CATATACTGC CTCCGCCATT TTTCCAATCA ATAATCGCTG GCGTATGATG
2521 GGTCAACTAC AATACGACTA CAACTTAGAT TATGTCATGG ATTCTTTGAT GGGGCTAAAT
2581 TATGAAGATT GCTGTTATGG TTTGTCAATC TATGCAAGAC GCTATCGTGA TGCTTTCAAT
2641 CCACATTTAT CACCTGATCA TGCAGTAATG GCAGAAGTTC GCCTAAACGG TATCGGTGGC
2701 GGCGGTCGTT TGAATCGACT TTTGAGCGAA AAGGTACTAG GCTATGATCA GGTTCGAAAT
2761 GCTTGGAGAC ATGATTACTA A (SEQ ID No : 1)
```

Figure 2

```
  1 MHTAHHHRSK TYLTTAIRYA LFGIASLPFV IPTYAELNTS RSLTVVGADS SKNLPDTPNT
 61 KPNTVLALDA HLQSHDDTAN AFDGFDFEVI TQQAAEQTSS QANQGNHQMS QLDAFASKSD
121 NPSLNTARLT DKHDTPSASK SLAKLAENYH IKSDPDAHRC QGMWMQPIHQ ATHTNRPTTP
181 KLDENGNPIT EDGIFAQADY GYYDAQTYAE LSGNVIMEQN GRRVTADKLT LDTQTGQATA
241 SGQVQFSDGG ASDHSAGIIG MAENLVYHTD GQTATAQDVA FASTTINAHG YASQMDKISS
301 SEYRLQHVMF TTCPPTERKW YLDTDSIDIN TDTGRAIAKN TTLRIKKVPV FYLPYFNFPI
361 DARRSSGFLL PSMGFGASDS FEISTPYYLN LAPDYDATIT PTVFTNRNPM LTGEFRYLTQ
421 DYGSGVLTAS YLPKDQQYHD KDRSRIQFDH TWQPKQFDKI TTYAQYQSVS DANYLSDFNA
481 LGVESAKLNL PRRIGTSFLD ENVSADLRFE DFQRLDGFGL DGRPITDKDR PYARLPQLSV
541 NYRLPRIWMG TPSGLELGGI HNSAYFKKSI KDNSEPEKSG GRIFNQFTAS YPLLRSWGYL
601 TPKLSLTHLY TSYDEDSLAD QNIAKKNGRH SVFAPTVSLD AGLFFEKAGA PFGMHQDTGG
661 YQVLTPRLHY TYTPFKDQHN VPNFETKIAQ LSYEQLLNNN WFLGHDRIQD LHAVTPAVSY
721 RYIDKMGRTR FEGGIAEQIL LSHIRVGIND SESYSSRSSG LAWQASLQPK DNLWFDASGS
781 FRTNYDLSSI VAQIRYRPSD RKLFNLGIVK RKENRAFNQS ALSAYTASAI FPINNRWRMM
841 GQLQYDYNLD YVMDSLMGLN YEDCCYGLSI YARRYRDAFN PHLSPDTAVM AEVRLNGIGG
901 GGRLNRLLSE KVLGYDQVRN AWRHDY* (SEQ ID No : 2)
```

Figure 3

```
  1 GTGGGTAAAA TTATGTCAAA AATTCCCATG ATGAATGAAA AGTATTTTCG TCGTCAGGCA
 61 CTTTATTGGT TGATTGCGGC GGCTATCATG GCAGGCTTGT GGTTGATTGT TTGGTTGACC
121 AGCTCCGTAC CAGCAATGAT TAATAAACAA AACGCCAATC AAACATCGTC CTATGTTGCG
181 ACATTGCCGA CCACAATCAC AGCGTTAAAT GAGCTTGATC ATGTTGTTAA GCCCATGGAT
241 AATTCGGCAC TTGTGCGAGA CTTACGCAAC TATCCACCTG AATTTAAGGA CAAAGTTTAT
301 TTTAATGGTA TTAGTGGTCG TTATACCATT GAGCTGATGG ATGTTACCGA AAATGAAGTT
361 ATCGTGGATT ATCTAAACAG CCGAGAAGAT CGTAACAATT TTGCTTATTT TCGCTATACT
421 GATGCCAATG ATAATAAGCG ATATGTACTG ACTTATGGTA AATTTACCAG TCCAGCTGAT
481 GCAGAATCTG CTTTGCAAAC CGTAAATTTT AGACTGCCAA AATCAGTGAT ACAAAAGACC
541 ACCAAAATCT CTGAGTTGGT CGCAGTAATG GACAATTATG AATTGGGTCA AGATGTGGTG
601 GATTTGGCAG ACTTCCAGCC TCGCCGAGTT CGCCTGCAAG CGACGCGTAC CGAAATTCCA
661 GTCAAAGCGG CCACGCCAGC AGATGAAGAA TTGGCACGCC TAAGCCGTGA GCGTGCATTA
721 CAAACACAAA TTTCCCAGCA AACTGAGTCG GTCAGGCAGC CGACTGATTT GGATATCCAA
781 AACGATATCA ATCGTTTGTC TAATCAAAGA TCTCAAGTCA GCTCTAGCGA TTTGCCTATG
841 GCACCAACTG CACGCCCACA GTCACCGCAG CAAACAGCCG ATATAGTACC CAAAAATGAA
901 ATATCTAAAG GCACTGCACC AACCCAAAGC CATTCGGCAG AGACAGAATC GCAATAA
(SEQ ID No : 3)
```

Figure 4

```
  1 VGKIMSKIPM MNEKYFRRQA LYWLIAAAIM AGLWLIVWLT SSVPAMINKQ NANQTSSYVA
 61 TLPTTITALN ELDHVVKPMD NSALVRDLRN YPPEFKDKVY FNGISGRYTI ELMDVTENEV
121 IVDYLNSRED RNNFAYFRYT DANDNKRYVL TYGKFTSPAD AESALQTVNF RLPKSVIQKT
181 TKISELVAVM DNYELGQDVV DLADFQPRRV RLQATRTEIP VKAATPADEE LARLSRERAL
241 QTQISQQTES VRQPTDLDIQ NDINRLSNQR SQVSSSDLPM APTARPQSPQ QTADIVPKNE
301 ISKGTAPTQS HSAETESQ* (SEQ ID No : 4)
```

MORAXELLA (BRANHAMELLA) CATARRHALIS POLYPEPTIDES AND CORRESPONDING DNA FRAGMENTS

FIELD OF THE INVENTION

The present invention is related to polypeptides, more particularly SMC-1 and SMC-2 polypeptides of *Moraxella (Branhamella) catarrhalis* which may be used to prevent, diagnose and/or treat *Moraxella (Branhamella) catarrhalis* infection.

BACKGROUND OF THE INVENTION

*Moraxella (Branhamella) catarrhalis* is a Gram-negative diplococcus that causes respiratory tract infections in humans. *M. catarrhalis* is now accepted as the third most common cause of otitis media in infants and children, after *Streptococcus pneumoniae* and *Haemophilus influenzae*. *M. catarrhalis* has also been associated with several other types of infection, including sinusitis, persistent cough, acute laryngitis, suppurative keratitis and conjunctivitis neonatorum.

Since approximately 90% of *M. catarrhalis* strains are resistant to antibiotics (β-lactamase positive) and that recurrent otitis media is associated with high morbidity, there is a need for the development of a vaccine that will protect hosts from *M. catarrhalis* infection. An infection by *M. catarrhalis* induces an immune response against antigens found at the surface of the bacterial cells. However, many of these surface proteins are still not characterized, nor has the immune response resulting in protection from infection by different strains been determined.

To develop a vaccine that will protect hosts from *M. catarrhalis* infection, efforts have mainly been concentrated on outer membrane proteins such as the high-molecular-mass protein named ubiquitous surface protein A (UspA). This protein is considered a promising vaccine candidate because a monoclonal antibody and polyclonal antibodies were both shown to be bactericidal and protective in the murine pulmonary-clearance model. However, this protein was shown to be highly variable among the different strains of *M. catarrhalis*. In addition to this protein, other *M. catarrhalis* proteins have generated interest as potential vaccine candidates. The transferrin-binding protein, which possesses conserved epitopes, exposed on the bacterial surface. However, there was divergence in the degree of antibody cross-reactivity with the protein from one strain to another. Other investigators have also focused on the 45-kDa protein CD (OMP CD). This protein is highly conserved among strains of *M. catarrhalis*, however adults with chronic obstructive pulmonary disease show variability in the immune response against the OMP CD.

Therefore there remains an unmet need for *M. catarrhalis* polypeptides that may be used to prevent, diagnose and/or treat *Moraxella (Branhamella) catarrhalis* infection.

SUMMARY OF THE INVENTION

According to one aspect, the present invention provides an isolated polynucleotide encoding a polypeptide having at least 70% identity to a second polypeptide comprising a sequence chosen from SEQ ID Nos: 2, 4 or fragments or analogs thereof.

According to one aspect, the present invention relates to polypeptides comprising a sequence chosen from SEQ ID No: 2, 4 or fragments or analogs thereof.

In other aspects, there are provided polypeptides encoded by polynucleotides of the invention, pharmaceutical compositions, vectors comprising polynucleotides of the invention operably linked to an expression control region, as well as host cells transfected with said vectors and processes for producing polypeptides comprising culturing said host cells under conditions suitable for expression.

BRIEF DESCRIPTION OF THE DRAWINGS

FIG. 1 represents the DNA sequence of SMC-1 gene from *M. catarrhalis* strain ETSU C-2; SEQ ID NOS: 1. The underlined portion of the sequence represents the region coding for the leader peptide.

FIG. 2 represents the amino acid sequence of SMC-1 polypeptide from *M. catarrhalis* strain ETSU C-2; SEQ ID NOS: 2. The underlined sequence represents the 35 amino acid residues leader peptide.

FIG. 3 represents the DNA sequence of SMC-2 gene from *M. catarrhalis* strain ETSU C-2; SEQ ID NO: 3. The underlined portion of the sequence represents the region coding for the leader peptide.

FIG. 4 represents the amino acid sequence of SMC-2 polypeptide from *M. catarrhalis* strain ETSU C-2; SEQ ID NO: 4. The underlined sequence represents the 47 amino acid residues leader peptide.

DETAILED DESCRIPTION OF THE INVENTION

The present invention provides purified and isolated polynucleotides, which encode *Moraxella* polypeptides which may be used to prevent, diagnose and/or treat *Moraxella* infection.

According to one aspect, the present invention provides an isolated polynucleotide encoding a polypeptide having at least 70% identity to a second polypeptide comprising a sequence chosen from SEQ ID NOS: 2, 4 or fragments or analogs thereof.

According to one aspect, the present invention provides an isolated polynucleotide encoding a polypeptide having at least 80% identity to a second polypeptide comprising a sequence chosen from SEQ ID NOS: 2, 4 or fragments or analogs thereof.

According to one aspect, the present invention provides an isolated polynucleotide encoding a polypeptide having at least 95% identity to a second polypeptide 2, 4 or fragments or analogs thereof.

According to one aspect, the present invention provides an isolated polynucleotide encoding a polypeptide having at least 98% identity to a second polypeptide 2, 4 or fragments or analogs thereof.

According to one aspect, the present invention provides an isolated polynucleotide encoding a polypeptide having at least 70% identity to a second polypeptide comprising SEQ ID NOS: 2 or 4.

According to one aspect, the present invention provides an isolated polynucleotide encoding a polypeptide having at least 80% identity to a second polypeptide comprising SEQ ID NOS: 2 or 4.

According to one aspect, the present invention provides an isolated polynucleotide encoding a polypeptide having at least 95% identity to a second polypeptide comprising SEQ ID NOS: 2 or 4.

According to one aspect, the present invention provides an isolated polynucleotide encoding a polypeptide having at least 98% identity to a second polypeptide comprising SEQ ID NOS: 2 or 4.

According to one aspect, the present invention relates to polypeptides which comprise an amino acid sequence selected from SEQ ID NOS: 2, 4 or fragments or analogs thereof.

According to one aspect, the present invention relates to polypeptides which comprise an amino acid sequence selected from SEQ ID NOS: 2 and 4.

According to one aspect, the present invention relates to polypeptides characterized by the amino acid sequence comprising SEQ ID NOS: 2, 4 or fragments or analogs thereof.

According to one aspect, the present invention relates to polypeptides characterized by the amino acid sequence comprising SEQ ID NOS: 2 or 4.

According to one aspect, the present invention provides a polynucleotide encoding an epitope bearing portion of a polypeptide comprising a sequence chosen from SEQ ID NOS: 2, 4 or fragments or analogs thereof.

According to one aspect, the present invention provides a polynucleotide encoding an epitope bearing portion of a polypeptide comprising a sequence chosen from SEQ ID NOS: 2 or 4.

According to one aspect, the present invention relates to epitope bearing portions of a polypeptide comprising a sequence chosen from SEQ ID NOS: 2, 4 or fragments or analogs thereof.

According to one aspect, the present invention relates to epitope bearing portions of a polypeptide comprising a sequence chosen from SEQ ID NOS: 2 or 4.

According to one aspect, the present invention provides an isolated polynucleotide comprising a polynucleotide chosen from:
(a) a polynucleotide encoding a polypeptide having at least 70% identity to a second polypeptide comprising a sequence chosen from: SEQ ID NOS: 2, 4 or fragments or analogs thereof;
(b) a polynucleotide encoding a polypeptide having at least 80% identity to a second polypeptide comprising a sequence chosen from: SEQ ID NOS: 2, 4 or fragments or analogs thereof;
(c) a polynucleotide encoding a polypeptide having at least 95% identity to a second polypeptide comprising a sequence chosen from: SEQ ID NOS: 2, 4 or fragments or analogs thereof;
(d) a polynucleotide encoding a polypeptide comprising a sequence chosen from: SEQ ID NOS: 2, 4 or fragments or analogs thereof;
(e) a polynucleotide encoding a polypeptide capable of raising antibodies having binding specificity for a polypeptide comprising a sequence chosen from: SEQ ID NOS: 2, 4 or fragments or analogs thereof;
(f) a polynucleotide encoding an epitope bearing portion of a polypeptide comprising a sequence chosen from SEQ ID NOS: 2, 4 or fragments or analogs thereof;
(g) a polynucleotide comprising a sequence chosen from SEQ ID NOS: 1, 3 or fragments or analogs thereof;
(h) a polynucleotide that is complementary to a polynucleotide in (a), (b), (c), (d), (e), (f) or (g).

According to one aspect, the present invention provides an isolated polynucleotide comprising a polynucleotide chosen from:
(a) a polynucleotide encoding a polypeptide having at least 70% identity to a second polypeptide comprising a sequence chosen from: SEQ ID NOS: 2 or 4;
(b) a polynucleotide encoding a polypeptide having at least 80% identity to a second polypeptide comprising a sequence chosen from: SEQ ID NOS: 2 or 4;
(c) a polynucleotide encoding a polypeptide having at least 95% identity to a second polypeptide comprising a sequence chosen from: SEQ ID NOS: 2 or 4;
(d) a polynucleotide encoding a polypeptide comprising a sequence chosen from: SEQ ID NOS: 2 or 4;
(e) a polynucleotide encoding a polypeptide capable of raising antibodies having binding specificity for a polypeptide comprising a sequence chosen from: SEQ ID NOS: 2 or 4;
(f) a polynucleotide encoding an epitope bearing portion of a polypeptide comprising a sequence chosen from SEQ ID NOS: 2 or 4;
(g) a polynucleotide comprising a sequence chosen from SEQ ID NOS: 1 or 3;
(h) a polynucleotide that is complementary to a polynucleotide in (a), (b), (c), (d), (e), (f) or (g).

According to one aspect, the present invention provides an isolated polypeptide comprising a polypeptide chosen from:
(a) a polypeptide having at least 70% identity to a second polypeptide comprising a sequence chosen from SEQ ID NOS: 2, 4 or fragments or analogs thereof;
(b) a polypeptide having at least 80% identity to a second polypeptide comprising a sequence chosen from SEQ ID NOS: 2, 4 or fragments or analogs thereof;
(c) a polypeptide having at least 95% identity to a second polypeptide comprising a sequence chosen from SEQ ID NOS: 2, 4 or fragments or analogs thereof;
(d) a polypeptide comprising a sequence chosen from SEQ ID NOS: 2, 4 or fragments or analogs thereof;
(e) a polypeptide capable of raising antibodies having binding specificity for a polypeptide comprising a sequence chosen from SEQ ID NOS: 2, 4 or fragments or analogs thereof;
(f) an epitope bearing portion of a polypeptide comprising a sequence chosen from SEQ ID NOS: 2, 4 or fragments or analogs thereof;
(g) the polypeptide of (a), (b), (c), (d), (e) or (f) wherein the N-terminal Met residue is deleted;
(h) the polypeptide of (a), (b), (c), (d), (e) or (f) wherein the secretory amino acid sequence is deleted.

According to one aspect, the present invention provides an isolated polypeptide comprising a polypeptide chosen from:
(a) a polypeptide having at least 70% identity to a second polypeptide comprising a sequence chosen from SEQ ID NOS: 2 or 4;
(b) a polypeptide having at least 80% identity to a second polypeptide comprising a sequence chosen from SEQ ID NOS: 2 or 4;
(c) a polypeptide having at least 95% identity to a second polypeptide comprising a sequence chosen from SEQ ID NOS: 2 or 4;
(d) a polypeptide comprising a sequence chosen from SEQ ID NOS: 2 or 4;
(e) a polypeptide capable of raising antibodies having binding specificity for a polypeptide comprising a sequence chosen from SEQ ID NOS: 2 or 4;
(f) an epitope bearing portion of a polypeptide comprising a sequence chosen from SEQ ID NOS: 2 or 4;
(g) the polypeptide of (a), (b), (c), (d), (e) or (f) wherein the N-terminal Met residue is deleted;
(h) the polypeptide of (a), (b), (c), (d), (e) or (f) wherein the secretory amino acid sequence is deleted.

Those skilled in the art will appreciate that the invention includes DNA molecules, i.e. polynucleotides and their complementary sequences that encode analogs such as mutants, variants, homologues and derivatives of such polypeptides, as described herein in the present patent application. The invention also includes RNA molecules corresponding to the DNA molecules of the invention. In addition to the DNA and RNA molecules, the invention includes the corresponding polypeptides and monospecific antibodies that specifically bind to such polypeptides.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a host.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The skilled person will appreciate that analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

As used herein, "fragments", "analogs" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 70% identity with those sequences illustrated in the figures or fragments thereof. That is, 70% of the residues are the same. In a further embodiment, polypeptides will have greater than 80% identity. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

These substitutions are those having a minimal influence on the secondary structure and hydropathic nature of the polypeptide. Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:

ala, pro, gly, gln, asn, ser, thr, val;
cys, ser, tyr, thr;
val, ile, leu, met, ala, phe;
lys, arg, orn, his;
and phe, tyr, trp, his.

The preferred substitutions also include substitutions of D-enantiomers for the corresponding L-amino acids.

In an alternative approach, the analogs could be fusion polypeptides, incorporating moieties which render purification easier, for example by effectively tagging the desired polypeptide. It may be necessary to remove the "tag" or it may be the case that the fusion polypeptide itself retains sufficient antigenicity to be useful.

The percentage of homology is defined as the sum of the percentage of identity plus the percentage of similarity or conservation of amino acid type.

In one embodiment, analogs of polypeptides of the invention will have about 70% homology with those sequences illustrated in the figures or fragments thereof. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, analogs of polypeptides of the invention will have fewer than about 20 amino acid residue substitutions, modifications or deletions and more preferably less than 10.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTX will align the longest stretch of similar sequences and assign a value to the fit. It is thus possible to obtain a comparison where several regions of similarity are found, each having a different score. Both types of identity analysis are contemplated in the present invention.

In an alternative approach, the analogs or derivatives could be fusion polypeptides, incorporating moieties which render purification easier, for example by effectively tagging the desired protein or polypeptide, it may be necessary to remove the "tag" or it may be the case that the fusion polypeptide itself retains sufficient antigenicity to be useful.

It is well known that it is possible to screen an antigenic polypeptide to identify epitopic regions, i.e. those regions which are responsible for the polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties.

In an additional aspect of the invention there are provided antigenic/immunogenic fragments of the proteins or polypeptides of the invention, or of analogs or derivatives thereof.

Thus, what is important for analogs, derivatives and fragments is that they possess at least a degree of the antigenicity/immunogenic of the protein or polypeptide from which they are derived.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *Moraxella* strains.

Moreover, the polypeptides of the present invention can be modified by terminal —$NH_2$ acylation (eg. by acetylation, or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments and analogs. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology.

In a further embodiment, the present invention also relates to chimeric polypeptides which comprise one or more polypeptides or fragments or analogs thereof as defined in the figures of the present application.

In a further embodiment, the present invention also relates to chimeric polypeptides comprising two or more polypeptides having a sequence chosen from SEQ ID NOS: 2, 4 or fragments or analogs thereof; provided that the polypeptides are linked as to form a chimeric polypeptide.

In a further embodiment, the present invention also relates to chimeric polypeptides comprising two or more polypeptides comprising a sequence chosen from SEQ ID NOS: 2 or 4 provided that the polypeptides are linked as to form a chimeric polypeptide.

Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different polypeptides may be a single bond or may be composed of a linking group of at least two, typically at least four, and not more than 16, but usually not more than about 14 carbon atoms.

In a particular embodiment, polypeptide fragments and analogs of the invention do not contain a starting residue, such as methionine (Met) or Valine (val). Preferably, polypeptides will not incorporate a leader or secretory sequence (signal sequence). The signal portion of a polypeptide of the invention may be determined according to established molecular biological techniques. In general, the polypeptide of interest may be isolated from a *Moraxella* culture and subsequently sequenced to determine the initial residue of the mature protein and therefore the sequence of the mature polypeptide.

It is understood that polypeptides can be produced and/or used without their start codon (methionine or valine) and/or without their leader peptide to favor production and purification of recombinant polypeptides. It is known that cloning genes without sequences encoding leader peptides will restrict the polypeptides to the cytoplasm of *E. coli* and will facilitate their recovery (Glick, B. R. and Pasternak, J. J. (1998) Manipulation of gene expression in prokaryotes. In "Molecular biotechnology: Principles and applications of recombinant DNA", 2nd edition, ASM Press, Washington DC, p.109-143).

According to another aspect of the invention, there are also provided (i) a composition of matter containing a polypeptide of the invention, together with a carrier, diluent or adjuvant; (ii) a pharmaceutical composition comprising a polypeptide of the invention and a pharmaceutically acceptable carrier, diluent or adjuvant; (iii) a vaccine comprising a polypeptide of the invention and a pharmaceutically acceptable carrier, diluent or adjuvant; (iv) a method for inducing an immune response against *Moraxella*, in a host, by administering to the host, an immunogenically effective amount of a polypeptide of the invention to elicit an immune response, e.g., a protective immune response to *Moraxella*; and particularly, (v) a method for preventing and/or treating a *Moraxella* infection, by administering a prophylactic or therapeutic amount of a polypeptide of the invention to a host in need.

According to another aspect of the invention, there are also provided (i) a composition of matter containing a polynucleotide of the invention, together with a carrier, diluent or adjuvant; (ii) a pharmaceutical composition comprising a polynucleotide of the invention and a pharmaceutically acceptable carrier, diluent or adjuvant; (iii) a method for inducing an immune response against *Moraxella*, in a host, by administering to the host, an immunogenically effective amount of a polynucleotide of the invention to elicit an immune response, e.g., a protective immune response to *Moraxella*; and particularly, (iv) a method for preventing and/or treating a *Moraxella* infection, by administering a prophylactic or therapeutic amount of a polynucleotide of the invention to a host in need.

Before immunization, the polypeptides of the invention can also be coupled or conjugated to carrier proteins such as tetanus toxin, diphtheria toxin, hepatitis B virus surface antigen, poliomyelitis virus VPl antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>> in Laboratory Techniques in Biochemistry and Molecular Biology, Vol.19 (ed.) Burdou, R. H. & Van Knippenberg P. H. (1988), Elsevier N.Y.

According to another aspect, there are provided pharmaceutical compositions comprising one or more *Moraxella* polypeptides of the invention in a mixture with a pharmaceutically acceptable adjuvant. Suitable adjuvants include (1) oil-in-water emulsion formulations such as MF59™, SAF™, Ribi™; (2) Freund's complete or incomplete adjuvant; (3) salts i.e. AlK(SO$_4$)$_2$, AlNa(SO$_4$)$_2$, AlNH$_4$(SO$_4$)$_2$, Al(OH)$_3$, AlPO$_4$, silica, kaolin; (4) saponin derivatives such as Stimulon™ or particles generated therefrom such as ISCOMs (immunostimulating complexes); (5) cytokines such as interleukins, interferons, macrophage colony stimulating factor (M-CSF), tumor necrosis factor (TNF); (6) other substances such as carbon polynucleotides i.e. poly IC and poly AU, detoxified cholera toxin (CTB)and *E.coli* heat labile toxin for induction of mucosal immunity. A more detailed description of adjuvant is available in a review by M. Z. I Khan et al. in Pharmaceutical Research, vol. 11, No. 1 (1994) pp2-11, and also in another review by Gupta et al., in Vaccine, Vol. 13, No. 14, pp1263-1276 (1995) and in WO 99/24578. Preferred adjuvants include QuilA™, QS21™, Alhydrogel™ and Adjuphos™.

Pharmaceutical compositions of the invention may be administered parenterally by injection, rapid infusion, nasopharyngeal absorption, dermoabsorption, or buccal or oral.

The term "pharmaceutical composition" is also meant to include antibodies. In accordance with the present invention, there is also provided the use of one or more antibodies having binding specificity for the polypeptides of the present invention for the treatment or prophylaxis of *Moraxella* infection and/or diseases and symptoms mediated by *Moraxella* infection.

Pharmaceutical compositions of the invention are used for the prophylaxis of *Moraxella* infection and/or diseases and symptoms mediated by *Moraxella* infection as described in Manual of Clinical Microbiology, P. R. Murray (Ed, in chief),E. J. Baron, M. A. Pfaller, F. C. Tenover and R. H. Yolken. ASM Press, Washington, D. C. seventh edition, 1999, 1773p. In one embodiment, pharmaceutical compositions of the present invention are used for the prophylactic or therapeutic treatment of otitis media, sinusitis, persistent cough, acute laryngitis, suppurative keratitis, conjunctivitis neonatorum and invasive diseases, comprising administering to the host a prophylactic or therapeutic amount of a composition of the invention. In one embodiment, pharmaceutical compositions of the invention are used for the treatment or prophylaxis of *Moraxella* infection and/or diseases and symptoms mediated by *Moraxella* infection. In a further embodiment, the *Moraxella* infection is *Moraxella Catarrhalis*.

In a further embodiment, the invention provides a method for prophylactic or therapeutic treatment of *Moraxella* infection in a host susceptible to *Moraxella* infection comprising administering to the host a prophylactic or therapeutic amount of a composition of the invention.

As used in the present application, the term "host" includes mammals. In a further embodiment, the mammal is human. In a further embodiment, the human is a neonate, infant or child. In a further embodiment, the human is an adult.

In a particular embodiment, pharmaceutical compositions are administered to those hosts at risk of *Moraxella* infection such as infants, elderly and immunocompromised hosts.

Pharmaceutical compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Pharmaceutical compositions are preferably in unit dosage form of about 0.1 µg to 10 mg and more preferably 1 µg to 1 mg and most preferably 10 to 100 µg 1 to 3 times with an interval of about 1 to 6 week intervals between immunizations.

According to another aspect, there are provided polynucleotides encoding polypeptides characterized by the amino acid sequence comprising SEQ ID NOS: 2, 4 or fragments or analogs thereof.

In one embodiment, polynucleotides are those illustrated in SEQ ID Nos: 1, 3 which may include the open reading frames (ORF), encoding the polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 70% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridization can be readily determined by one of skilled in the art (see for example Sambrook et al., (1989) Molecular cloning: A Laboratory Manual, 2$^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridize under stringent conditions to either (a) a DNA sequence encoding a polypeptide or
(b) the complement of a DNA sequence encoding a polypeptide;

wherein said polypeptide comprises a sequence chosen from SEQ ID NOS: 2, 4 or fragments or analogs thereof.

In a further embodiment, the present invention provides polynucleotides that hybridize under stringent conditions to either (a) a DNA sequence encoding a polypeptide or
(b) the complement of a DNA sequence encoding a olypeptide;

wherein said polypeptide comprises a sequence chosen from SEQ ID NOS: 2 or 4.

In a further embodiment, the present invention provides polynucleotides that hybridize under stringent conditions to either (a) a DNA sequence encoding a polypeptide or
(b) the complement of a DNA sequence encoding a polypeptide;

wherein said polypeptide comprises at least 10 contiguous amino acid residues from a polypeptide comprising a sequence chosen from SEQ ID NOS: 2, 4 or fragments or analogs thereof.

In a further embodiment, the present invention provides polynucleotides that hybridize under stringent conditions to either (a) DNA sequence encoding a polypeptide or
(b) the complement of a DNA sequence encoding a polypeptide;

wherein said polypeptide comprises at least 10 contiguous amino acid residues from a polypeptide comprising a sequence chosen from SEQ ID NOS: 2 or 4.

In a further embodiment, polynucleotides are those encoding polypeptides of the invention illustrated in SEQ ID NOS: 2, 4.

In a further embodiment, polynucleotides are those illustrated in SEQ ID NOS: 1, 3 encoding polypeptides of the invention.

As will be readily appreciated by one skilled in the art, polynucleotides include both DNA and RNA.

The present invention also includes polynucleotides complementary to the polynucleotides described in the present application.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N. J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York.

The present invention provides host cells transfected with vectors comprising the polynucleotides of the invention.

The present invention provides a process for producing a polypeptide comprising culturing a host cell of the invention under conditions suitable for expression of said polypeptide.

For recombinant production, host cells are transfected with vectors which encode the polypeptides of the invention, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York). Suitable promoters include but are not limited to LTR or SV40 promoter, *E. coli* lac, tac or trp promoters and the phage lambda $P_L$ promoter. Vectors will preferably incorporate an origin of replication as well as selection markers i.e. ampicilin resistance gene. Suitable bacterial vectors include pET, pQE70, pQE60, pQE-9, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and PSVL. Host cells may be. bacterial i.e. *E.coli, Bacillus subtilis, Strepto-*

*myces*; fungal i.e. *Aspergillus niger, Aspergillus nidulins*; yeast i.e. *Saccharomyces* or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptides may be expressed with or without a leader or secretion sequence. In the former case the leader may be removed using post-translational processing (see U.S. Pat. Nos. 4,431,739; 4,425,437; and 4,338,397) or be chemically removed subsequent to purifying the expressed polypeptide.

According to a further aspect, the *Moraxella* polypeptides of the invention may be used in a diagnostic test for *Moraxella* infection, in particular *Moraxella* infection.

Several diagnostic methods are possible, for example detecting *Moraxella* organism in a biological sample, or for diagnostic of a *Moraxella* infection in an host susceptible to *Moraxella* infection, the following procedure may be followed:
a) obtaining a biological sample from a host;
b) incubating an antibody or fragment thereof reactive with a *Moraxella* polypeptide of the invention with the biological sample to form a mixture; and
c) detecting specifically bound antibody or bound fragment in the mixture which indicates the presence of *Moraxella*.

Alternatively, a method for the detection of antibody specific to a *Moraxella* antigen in a biological sample containing or suspected of containing said antibody may be performed as follows:
a) obtaining a biological sample from a host;
b) incubating one or more *Moraxella* polypeptides of the invention or fragments thereof with the biological sample to form a mixture; and
c) detecting specifically bound antigen or bound fragment in the mixture which indicates the presence of antibody specific to *Moraxella*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences encoding polypeptides of the invention may also be used to design DNA probes for use in detecting the presence of *Moraxella* in a biological sample suspected of containing such bacteria. The detection method of this invention comprises:
a) obtaining the biological sample from a host;
b) incubating one or more DNA probes having a DNA sequence encoding a polypeptide of the invention or fragments thereof with the biological sample to form a mixture; and
c) detecting specifically bound DNA probe in the mixture which indicates the presence of *Moraxella* bacteria.

The DNA probes of this invention may also be used for detecting circulating *Moraxella* i.e. *Moraxella* nucleic acids in a sample, for example using a polymerase chain reaction, as a method of diagnosing *Moraxella* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *Moraxella* polypeptides of the invention. In a further embodiment, the preferred DNA probe will be an oligomer having a sequence complementary to at least about 15 contiguous nucleotides of the *Moraxella* polypeptides of the invention. In a further embodiment, the preferred DNA probe will be an oligomer having a sequence complementary to at least about 30 contiguous nucleotides of the *Moraxella* polypeptides of the invention. In a further embodiment, the preferred DNA probe will be an oligomer having a sequence complementary to at least about 50 contiguous nucleotides of the *Moraxella* polypeptides of the invention.

Another diagnostic method for the detection of *Moraxella* in a host comprises:
a) labelling an antibody reactive with a polypeptide of the invention or fragment thereof with a detectable label;
b) administering the labelled antibody or labelled fragment to the host; and
c) detecting specifically bound labelled antibody or labelled fragment in the host which indicates the presence of *Moraxella*.

A further aspect of the invention is the use of the *Moraxella* polypeptides of the invention as immunogens for the production of specific antibodies for the diagnosis and in particular the treatment of *Moraxella* infection. Suitable antibodies may be determined using appropriate screening methods, for example by measuring the ability of a particular antibody to passively protect against *Moraxella* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Moraxella* polypeptides but is preferably specific for one.

According to one aspect, the present invention provides the use of an antibody for prophylaxis and/or treatment of *Moraxella* infection.

In a further aspect, the invention provides a method for prophylactic or therapeutic treatment of *Moraxella* infection in a host susceptible to *Moraxella* infection comprising administering to the host a prophylactic or therapeutic amount of a pharmaceutical composition of the invention.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

A further aspect of the invention is the use of the antibodies directed to the polypeptides of the invention for passive immunization, whereby an antibody raised by a polypeptide of the invention is administered to a host in an amount sufficient to provide a passive immunization. One could use the antibodies described in the present application. Suitable antibodies may be determined using appropriate screening methods, for example by measuring the ability of a particular antibody to passively protect against *Moraxella* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Moraxella* polypeptides but is preferably specific for one.

The use of a polynucleotide of the invention in genetic immunization will preferably employ a suitable delivery method or system such as direct injection of plasmid DNA into muscles [Wolf et al. H M G (1992) 1: 363; Turnes et al., Vaccine (1999), 17: 2089; Le et al., Vaccine (2000) 18: 1893; Alves et al., Vaccine (2001) 19: 788], injection of plasmid DNA with or without adjuvants [Ulmer et al., Vaccine (1999) 18: 18; MacLaughlin et al., J. Control Release (1998) 56: 259; Hartikka et al., Gene Ther. (2000) 7: 1171-82; Benvenisty and Reshef, PNAS USA (1986) 83:9551; Singh et al., PNAS USA (2000) 97: 811], targeting cells by delivery of DNA complexed with specific carriers [Wa et al., J Biol Chem (1989) 264: 16985; Chaplin et al., Infect. Immun. (1999) 67: 6434], injection of plasmid complexed or encapsulated in various forms of liposomes [Ishii et al., AIDS Research and Human Retroviruses (1997) 13: 142; Perrie et al., Vaccine (2001) 19: 3301], administration of DNA with different methods of bombardment [Tang et al., Nature (1992) 356: 152; Eisenbraun et al., DNA Cell Biol (1993) 12: 791; Chen et al., Vaccine (2001) 19: 2908], and administration of DNA with lived vectors [Tubulekas et al., Gene (1997) 190: 191; Pushko et al., Virology (1997) 239: 389; Spreng et al. FEMS (2000) 27: 299; Dietrich et al., Vaccine (2001) 19: 2506].

According to one aspect, the present invention provides the use of an antibody for prophylaxis and/or treatment of *Moraxella* infections.

In a further embodiment, the invention provides the use of a pharmaceutical composition of the invention in the manufacture of a medicament for the prophylactic or therapeutic treatment of *Moraxella* infection.

In a further embodiment, the invention provides a kit comprising a polypeptide of the invention for detection or diagnosis of *Moraxella* infection.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

This example illustrates the cloning and molecular characteristics of SMC-1 gene and corresponding polypeptide.

The coding region of *M. catarrhalis* SMC-1 (SEQ ID NO: 1) gene was amplified by PCR (DNA Thermal Cycler GeneAmp PCR system 2400 Perkin Elmer, San Jose, Calif.) from genomic DNA of *M. catarrhalis* strain ETSU C-2 using the following oligos that contained base extensions for the addition of restriction sites NcoI (CCATGG) and XhoI (CTCGAG): RIOS30 (5'-TATGTACCATGGCTGAACT-CAATACCAGCCGTTCA-3')(SEQ ID NO: 13) and RIOS31 (5'-GGCATGCTCGAGGTAATCATGTCTC-CAAGCATTTTG-3')(SEQ ID NO: 14). PCR products were purified from agarose gel using a QIA®quick gel extraction kit following the manufacturer's instructions (Qiagen®, Chatsworth, Calif.), and digested with NcoI and XhoI (Amersham Pharmacia Biotech, Inc, Baie d'Urf, Canada). The pET21d(+) vector (Novagen®, Madison, Wis.) was digested with NcoI and XhoI and purified from agarose gel using a QIA®quick extraction kit (Qiagen®). The NcoI-XhoI PCR products were ligated to the NcoI-XhoI pET21d(+) expression vector. The ligated products were transformed into *E. coli* strain DH5α Φ80dlacZΔM15 Δ(lacZYA-argF) U169 endA1 recA1 hsdR17($r_K^-$–$m_K^-$+) deoR thi-1 supE44 λ$^-$gyrA96 relA1] (Gibco BRL, Gaithersburg, Md.) according to the method of Simanis (Hanahan, D. DNA Cloning, 1985, D. M. Glover (ed), pp. 109-135). Recombinant pET21d(+) plasmid (rpET21d(+)) containing SMC-1 gene was purified using a Qiagen® kit and DNA insert was sequenced (Taq Dye Deoxy Terminator Cycle Sequencing kit, ABI, Foster City, Calif.).

TABLE 1

Oligonucleotide primers used for PCR amplification of *M. catarrhalis* genes.

| Genes | Primers I.D. | Restriction site | Vector | Sequence (SEQ ID No) |
|---|---|---|---|---|
| SMC-1 | RIOS30 | NcoI | pET21d (+) | 5'-TATGTACCATGGCTGAACTCAATACCAGCCGTTCA-3' (SEQ ID No:5) |
| SMC-1 | RIOS31 | XhoI | pET21d (+) | 5'-GGCATGCTCGAGGTAATCATGTCTCCAAGCATTTTG-3' (SEQ ID No:6) |
| SMC-1 | RIOS187 | BglII | pCMV-GH | 5'-GGCAGATCTTGGAACTCAATACCAGCCGTTC-3' (SEQ ID No:7) |
| SMC-1 | RIOS188 | SalI | pCMV-GH | 5'-ACGCGTCGACTTAGTAATCATGTCTCCAAGCAT-3' (SEQ ID No:8) |
| SMC-2 | RIOS20 | NdeI | pET21b (+) | 5'-CGTACCAGCACATATGAATAAACAAAACGCCAATCAA-3' (SEQ ID No :9) |
| SMC-2 | RIOS21 | XhoI | pET21b (+) | 5'-GCCCATCTCGAGTTGCGATTCTGTCTCTGCC-3' (SEQ ID No:10) |
| SMC-2 | RIOS189 | BamHI | pCMV-GH | 5'-CGAGGATCCTAATAAACAAAACGCCAATCAAAC-3' (SEQ ID No:11) |
| SMC-2 | RIOS190 | HindIII | pCMV-GH | 5'-CAGAAGCTTTTATTGCGATTCTGTCTCTGCC-3' (SEQ ID No:12) |

It was determined that the open reading frame (ORF) which codes for SMC-1 polypeptide contains 2781-bp and encodes a 926 amino acid residues polypeptide with a predicted pI of 6.31 and a predicted molecular mass of 104054.84 Da. Analysis of the predicted amino acid residues sequence (SEQ ID NO:2) using the Spscan software (Wisconsin Sequence Analysis Package; Genetics Computer Group) suggested the existence of a 35 amino acid residues signal peptide (MHTAHHHRSKTYLTTAIRYALF-GIASLPFVIPTYA)(SEQ ID NO: 15), which ends with a cleavage site located between an alanine and a glutamic acid residues.

To confirm the presence by PCR amplification of SMC-1 (SEQ ID NO: 1) gene, the following 3 distinct *M. catarrhalis* strains were used: *M. catarrhalis* ETSU C-2, ETSU T-25, and ETSU 658 clinical isolates were provided by the East Tennessee State University. The *E. coli* XL1-Blue MRF' was used in these experiments as negative control. SMC-1 (SEQ ID NO :1) gene was amplified by PCR (DNA Thermal Cycler GeneAmp PCR system 2400 Perkin Elmer) from genomic DNA from the 3 *M. catarrhalis* strains, and the control *E. coli* strain using the oligonucleotides primers RIOS30 and RIOS31 (Table 1). PCR was performed with 5 cycles of 15 sec at 94° C., 30 sec at 47° C. and 3 min at 68° C. followed by 30 cycles of 15 sec at 94° C., 30 sec at 63° C. and 3 min at 68° C. and a final elongation period of 5 min at 68° C. The PCR products were size fractionated in 1% agarose gels and were visualized by ethidium bromide staining. The results of these PCR amplifications are presented in Table 2. The analysis of the amplification products revealed that SMC-1 (SEQ ID NO :1) gene was present in the genome of all of the 3 *M. catarrhalis* strains tested. No such product was detected when the control *E. coli* DNA was submitted to identical PCR amplifications with these oligonucleotide primers.

TABLE 2

Identification of *M. catarrhalis* genes by PCR amplification.

| Strain Identification | Identification by PCR amplification of | |
|---|---|---|
| | SMC-1 | SMC-2 |
| ETSU C-2 | + | + |
| ETSU 658 | + | + |
| ETSU T-25 | + | + |
| *E. coli* | − | − |

EXAMPLE 2

This example illustrates the cloning and molecular characteristics of SMC-2 gene and corresponding polypeptide.

The coding region of *M. catarrhalis* SMC-2 (SEQ ID NO: 3) gene was amplified by PCR (DNA Thermal Cycler GeneAmp PCR system 2400 Perkin Elmer) from genomic DNA of *M. catarrhalis* strain ETSU C-2 using the following oligos that contained base extensions for the addition of restriction sites NdeI (CATATG) and XhoI (CTCGAG): RIOS20 and RIOS21, which are presented in Table 1. The methods used for cloning SMC-2 gene into an expression vector and sequencing are similar to the methods described in Example 1.

It was determined that the open reading frame (ORF) which codes for SMC-2 contains 957-bp and encodes a 318 amino acid residues polypeptide with a predicted pI of 5.78 and a predicted molecular mass of 35954.10 Da. Analysis of the predicted amino acid residues sequence (SEQ ID NO:4) using the Spscan software (Wisconsin Sequence Analysis Package; Genetics Computer Group) suggested the existence of a 47 amino acid residues signal peptide (VGKIMSKIPMMNEKYFRRQALYWLIAAAIMAGL-WLIVWLTSSVPAMI) (SEQ ID NO: 16), which ends with a cleavage site located between an isoleucine and an asparagine residues.

The SMC-2 gene was shown to be present after PCR amplification using the oligonucleotide primers RIOS20 and RIOS21 in the 3 *M. catarrhalis* strains tested (Table 2). The methods used for PCR amplification of the SMC-2 gene were similar to the methods presented in Example 1. No such product was detected when the control *E. coli* DNA was submitted to identical PCR amplification with these oligonucleotide primers.

EXAMPLE 3

This example illustrates the cloning of *M. catarrhalis* genes in CMV plasmid pCMV-GH.

The DNA coding regions of *M. catarrhalis* polypeptides were inserted in phase downstream of a human growth hormone (hGH) gene which was under the transcriptional control of the cytomegalovirus (CMV) promotor in the plasmid vector pCMV-GH (Tang et al., Nature, 1992, 356: 152). The CMV promotor is non-functional plasmid in *E. coli* cells but active upon administration of the plasmid in eukaryotic cells. The vector also incorporated the ampicillin resistance gene.

The coding regions of SMC-1 (SEQ ID NO: 1) and SMC-2 (SEQ ID NO: 3) genes without their leader peptide regions were amplified by PCR (DNA Thermal Cycler GeneAmp PCR system 2400 Perkin Elmer) from genomic DNA of *M. catarrhalis* strain ETSU C-2 using oligonucleotide primers that contained base extensions for the addition of restriction sites BamHI (GGATCC), BglII (AGATCT), SalI (GTCGAC), or HindIII (AAGCTT) which are described in Table 1. The PCR products were purified from agarose gel using a QIAquick gel extraction kit (Qiagen), and digested with restriction enzymes (Amersham Pharmacia Biotech, Inc). The pCMV-GH vector (Laboratory of Dr. Stephen A. Johnston, Department of Biochemistry, The University of Texas, Dallas, Tex.) was digested with BamHI, BglII, SalI, or HindIII and purified from agarose gel using the QIAquick gel extraction kit (Qiagen). The digested DNA fragments were ligated to the digested pCMV-GH vector to create the hGH-SMC-1 and hGH-SMC-2 fusion polypeptides under the control of the CMV promoter. The ligated products were transformed into *E. coli* strain DH5α [φ80dlacZΔM15 Δ(lacZYA-argF) U169 endα1 recA1 hsdR17 ($r_K$–$m_K$+) deoR thi-1 supE44λ⁻-gyrA96 relA1] (Gibco BRL) according to the method of Simanis (Hanahan, D. DNA Cloning, 1985, D. M. Glover (ed), pp. 109-135). The recombinant pCMV plasmids were purified using a Qiagen kit, and the nucleotide sequences of the DNA inserts were verified by DNA sequencing.

EXAMPLE 4

This example illustrates the use of DNA to elicit an immune response to *M. catarrhalis* polypeptide antigens.

A group of 8 female BALB/c mice (Charles River, St-Constant, Québec, Canada) were immunized by intramuscular injection of 100 μl three times at two- or three-week intervals with 50 μg of recombinant pCMV-GH encoding SMC-1 (SEQ ID NO: 1) and SMC-2 (SEQ ID NO: 3) genes in presence of 50 μg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, a group of mice were injected with 50 μg of pCMV-GH in presence of 50 μg of pCMV-GH-GM-CSF. Blood samples were collected from the orbital sinus prior to each immunization and seven days following the third injection. Serum antibody responses were determined by ELISA using the corresponding His-Tag labeled *M. catarrhalis* recombinant polypeptides as coating antigen. The production and purification of these His-tag labeled *M. catarrhalis* recombinant polypeptides are presented in Example 5.

EXAMPLE 5

This example illustrates the production and purification of M. catarrhalis recombinant polypeptides.

The recombinant pET21 plasmid with SMC-1 (SEQ ID NO: 1) and SMC-2 (SEQ ID NO: 3) genes were used to transform by electroporation (Gene Pulser II apparatus, BIO-RAD Labs, Mississauga, Canada) E. coli strain AD494 (DE3) [Δara-leu7697 ΔlacX74 ΔphoA PvuII phoR ΔmalF3 F' [lac$^+$(lacI$^q$) pro] trxB::Kan (DE3)] (Novagen). In this strain of E. coli, the T7 promotor controlling expression of the recombinant polypeptide is specifically recognized by the T7 RNA polymerase (present on the λDE3 prophage) whose gene is under the control of the lac promotor which is inducible by isopropyl-β-d-thio-galactopyranoside (IPTG). The transformant AD494(DE3)/rpET21 was grown at 37° C. with agitation at 250 rpm in LB broth (peptone 10 g/L, yeast extract 5 g/L, NaCl 10 g/L) containing 100 μg of carbenicillin (Sigma-Aldrich Canada Ltd., Oakville, Canada) per ml until the $A_{600}$ reached a value of 0.5. In order to induce the production of His-tagged M. catarrhalis recombinant polypeptides, the cells were incubated for 3 additional hours in the presence of IPTG at a final concentration of 1 mM. Induced cells from a 500 ml culture were pelleted by centrifugation and frozen at −70° C.

The purification of the recombinant polypeptides from the soluble cytoplasmic fraction of IPTG-induced AD494 (DE3)/rpET21 was done by affinity chromatography based on the properties of the His.Tag sequence (6 consecutive histidine residues) to bind to divalent cations ($Ni^{2+}$) immobilized on the His.Bind metal chelation resin. Briefly, the pelleted cells obtained from a 500 mL culture induced with IPTG was resuspended in lysis buffer (20 mM Tris, 500 mM NaCl, 10 mM imidazole, pH 7.9) containing 1 mM PMSF, sonicated and centrifuged at 12,000 X g for 20 min to remove debris. The supernatant was deposited on a Ni-NTA agarose column (Qiagen). The His-tag labeled M. catarrhalis recombinant polypeptides were eluted with 250 mM imidazole-500 mM NaCl-20 mM Tris pH 7.9. The removal of the salt and imidazole from the sample was done by dialysis against PBS at 4° C. The quantities of recombinant polypeptides obtained from the soluble fraction of E. coli was estimated by MicroBCA (Pierce, Rockford, Ill.).

EXAMPLE 6

This example illustrates the reactivity of the His-tagged M. catarrhalis recombinant polypeptides with antibodies present in human palatine tonsils.

As shown in Table 3, SMC-1 and SMC-2 His-tagged recombinant polypeptide were recognized in immunoblots by the antibodies present in the human palatine tonsils. It indicates that humans, which are normally in contact with M. catarrhalis do develop antibodies that are specific to these polypeptides. These particular human antibodies might be implicated in the protection against M. catarrhalis infection.

TABLE 3

Reactivity in immunoblots of antibodies present in human palatine tonsils with M. catarrhalis His-tagged fusion recombinant polypeptides.

| Purified recombinant polypeptide I.D.[1] | Apparent molecular weight (kDa)[2] | Reactivity in immunoblots with antibodies present in human palatine tonsils[3] |
|---|---|---|
| SMC-1 | 104 | + |
| SMC-2 | 36 | + |

[1]His-tagged recombinant polypeptides produced and purified as described in Example 5 were used to perform the immunoblots.
[2]Molecular weight of the His-tagged recombinant polypeptide was estimated after SDS-PAGE.
[3]Extracts from human palatine tonsils were not diluted in order to perform the immunoblots.

EXAMPLE 7

This example illustrates the accessibility to antibodies of the SMC-1 and SMC-2 polypeptides at the surface of M. catarrhalis strain.

Bacteria were grown in Brain Heart Infusion (BHI) broth containing 1% dextrose at 37° C. in a 8% $CO_2$ atmosphere to give an $OD_{490nm}$ of 0.650 (~$10^8$ CFU/ml). Dilutions of anti-SMC-1 or anti-SMC-2 or control sera were then added and allowed to bind to the cells, which were incubated for 2 h at 4° C. with rotation. Samples were washed 4 times in blocking buffer [phosphate-buffered saline (PBS) containing 2% bovine serum albumin (BSA)], and then 1 ml of goat fluorescein (FITC)-conjugated anti-mouse IgG Fc (gamma) fragment specific diluted in blocking buffer was added. After an additional incubation of 60 min at room temperature with rotation in the dark, samples were washed 4 times in blocking buffer and fixed with 0.25% formaldehyde in PBS buffer for 18 h at 4° C. Cells were centrifuged and resuspended in 0.5 ml of PBS buffer. Cells were kept in the dark at 4° C. until analyzed by flow cytometry (Epics® XL; Beckman Coulter, Inc.). Flow cytometric analysis revealed that SMC-1- and SMC-2-specific antibodies efficiently recognized their corresponding surface exposed epitopes on the homologous (ETSU C-2) M. catarrhalis strain tested (Table 4). It was determined that more than 89% of the 10,000 Moraxella cells analyzed were labeled with the antibodies present in the SMC-1- and SMC-2-specific sera. In addition, antibodies present in the pool of SMC-1- and SMC-2-specific sera attached at the surface of ETSU 658 strain of M. catarrhalis (Table 4). It was also determined that more than 90% of the 10,000 cells of this strain were labeled by the specific antibodies. These observations clearly demonstrate that the SMC-1 and SMC-2 polypeptides are accessible at the surface, where they can be easily recognized by antibodies. Anti-M. catarrhalis antibodies were shown to play an important role in the protection against M. catarrhalis infection.

TABLE 4

Evaluation of the attachment of SMC-1- and SMC-2-specific antibodies at the surface of intact cells of M. catarrhalis.

| Serum Identification | Strains | Fluorescence Index[2] | % of labeled cells[3] |
|---|---|---|---|
| Pool of SMC-1-specific sera[1] | ETSU C-2 | 19.8 | 96.1 |
| | ETSU 658 | 15.2 | 93.1 |

TABLE 4-continued

Evaluation of the attachment of SMC-1- and SMC-2-specific antibodies at the surface of intact cells of *M. catarrhalis*.

| Serum Identification | Strains | Fluorescence Index[2] | % of labeled cells[3] |
|---|---|---|---|
| Pool of SMC-2-specific sera | ETSU C-2 | 11.0 | 89.8 |
|  | ETSU 658 | 11.9 | 90.5 |
| Pool of negative control sera[4] | ETSU C-2 | 1.0 | 1.0 |
|  | ETSU 658 | 1.0 | 1.0 |
| Positive control serum[5] | ETSU C-2 | 25.0 | 97.4 |
|  | ETSU 658 | 19.6 | 93.3 |

[1]The mice were injected subcutaneously five times at two-week intervals with 20 µg of purified recombinant polypeptides mixed with 10 µg of QuilA adjuvant (Cedarlane Laboratories, Hornby, Canada). The sera were diluted 1/50.
[2]The fluorescence index was calculated as the median fluorescence value obtained after labeling the cells with an immune serum divided by the fluorescence value obtained for a control mouse serum. A fluorescence value of 1 indicated that there was no binding of antibodies at the surface of intact Moraxella cells.
[3]% of labeled cells out of the 10,000 cells analyzed.
[4]Sera collected from unimmunized or sham-immunized mice were pooled, diluted 1/50, and used as negative controls for this assay.
[5]Serum obtained from a mouse immunized with 20 µg of purified outer membrane polypeptides from *M. catarrhalis* strain ETSU-C2 was diluted 1/1000 and was used as a positive control for the assay.

EXAMPLE 8

This example illustrates the bactericidal activities of anti-SMC-1 and anti-SMC-2 mouse sera.

Bacteria are plated on chocolate agar plate and incubated at 37° C. in a 8% $CO_2$ atmosphere for 16 h. Bacterial cells are then resuspended in bacteriolysis buffer [10% Hanks' Balanced Salt Solution (HBSS) and 1% hydrolyzed casein, pH 7.3] to an $OD_{490nm}$ of 0.25 and diluted to $8 \times 10^4$ CFU/ml. The bactericidal assay is performed by mixing 25 µl of the bacterial suspension with 50 µl of diluted heat-inactivated test serum and 15 µl of HBSS and incubating for 15 min at 37° C., 8% $CO_2$ with agitation (200 rpm). The rabbit complement-containing serum is then added to a final concentration of 10%, and the mixture is incubated for an additional 60 min at 37° C., 8% $CO_2$ with agitation (200 rpm). At the end of the incubation period, the number of viable bacteria is determined by plating 10 µl of the assay mixture on chocolate agar plate. The plates are incubated at 37° C. in an 8% $CO_2$ atmosphere for 18-24 h. The control consists of bacteria incubated with heat-inactivated sera collected from mice before immunization and rabbit complement. The bactericidal titer is determined as the highest serum dilution resulting in killing of 50% or more of the bacteria compared to the control. The *M. catarrhalis* strain ETSU 658 is used to evaluate the bactericidal activity of the sera. Bactericidal activity against *M. catarrhalis* strain ETSU 658 is detected in sera collected from mice immunized five times with 20 µg of recombinant SMC-1 or SMC-2 polypeptides.

EXAMPLE 9

This example illustrates the protection of mice against *M. catarrhalis* infection induced by immunization.

Groups of 10 female BALB/c mice (Charles River) are immunized subcutaneously five times at two-week intervals with 20 µg of affinity purified His-tagged *M. catarrhalis* recombinant polypeptides in presence of 10% of QuilA adjuvant (Cedarlane Laboratories Ltd) or, as control, with QuilA adjuvant alone in PBS. Blood samples are collected from the orbital sinus on day 0, 14, 28, 42, and 56 prior to each immunization and 14 days (day 70) following the fifth injection. One week later the mice are challenged intrapulmonary with approximately $1 \times 10^6$ CFU of the *M. catarrhalis* strain ETSU 658. Samples of the *M. catarrhalis* challenge inoculum are plated on chocolate agar plates to determine the CFU and to verify the challenge dose. Mice are killed by an intraperitoneal injection of sodium pentobarbital (Euthanyl™) 5 h after infection. The intact lungs are excised and homogenised in a tissue homogeniser. The lung homogenate is assessed for bacterial clearance by plating of serial dilutions for CFU determination.

The invention claimed is:

1. An isolated polypeptide comprising
   (a) an amino acid sequence at least 90% identical to the amino acid sequence set forth in SEQ ID NO:2; or
   (b) an amino acid sequence at least 95% identical to the amino acid sequence set forth in SEQ ID NO:2,
   wherein the polypeptide is capable of raising antibodies that specifically bind to the polypeptide comprising the amino acid sequence set forth in SEQ ID NO:2.

2. An isolated polypeptide comprising:
   (a) the amino acid sequence set forth in SEQ ID NO:2;
   (b) the polypeptide of (a), wherein the N-terminal methionine residue is deleted; or
   (c) the polypeptide of (a), wherein the signal peptide amino acid sequence is deleted.

3. A pharmaceutical composition comprising a polypeptide according to either claim 1 or claim 2 and a pharmaceutically acceptable carrier, diluent or adjuvant.

4. A method for inducing an immune response against *Moraxella catarrhalis* in a host comprising administering to said host the composition according to claim 3.

5. A method according to claim 4 wherein the host is a neonate, an infant or a child.

6. A method according to claim 4 wherein the host is an immunocompromised host.

7. A method according to claim 4 wherein the host is an adult.

8. A method of diagnosing *Moraxella catarrhalis* infection in a host susceptible to *Moraxella catarrhalis* infection comprising:
   (a) obtaining a biological sample from a host;
   (b) incubating one or more polypeptides according to either claim 1 or claim 2 with the biological sample to form a mixture; and
   (c) detecting specifically bound polypeptide in the mixture which indicates the presence of an antibody that specifically binds to the *Moraxella catarrhalis* antigen thereby detecting *Moraxella catarrhalis* infection.

9. A method for the detection of an antibody that specifically binds to a *Moraxella catarrhalis* antigen in a biological sample containing or suspected of containing said antibody comprising:
   (a) obtaining a biological sample from a host;
   (b) incubating one or more polypeptides according to either claim 1 or claim 2 with the biological sample to form a mixture, and
   (c) detecting specifically bound polypeptide in the mixture which indicates the presence of an antibody that specifically binds to the *Moraxella catarrhalis* antigen.

10. A kit comprising the polypeptide according to either claim 1 or claim 2 for detection or dialgnosis of *Moraxella catarrhalis* infection.

* * * * *

SEQUENCE LISTING

```
<160> NUMBER OF SEQ ID NOS: 14

<210> SEQ ID NO 1
<211> LENGTH: 2781
<212> TYPE: DNA
<213> ORGANISM: Moraxella catarrhalis

<400> SEQUENCE: 1
atgcacaccg ctcatcacca tcgctcaaag acatatttga ctaccgctat tcgttacgca      60
ctatttggta tcgccagttt gccatttgtc ataccaactt atgcagaact caataccagc     120
cgttcactga cagtcgttgg tgctgacagc tcaaaaaatt tgcctgatac accaaatacc     180
aaacccaata ctgtcttagc cttagacgcc catctacaaa gtcatgatga tactgccaat     240
gcctttgatg gctttgattt tgaagttatc acacagcagg cagccgagca gacaagcagt     300
caagcaaatc aaggcaatca tcagatgagc cagcttgacg cctttgctag taagtcagac     360
aatccaagtt taaacactgc caggctgacg gataagcatg atacaccctc tgccagtaaa     420
agcttagcca aattagccga aaactaccat attaagtccg atccagacgc tcatcgttgt     480
```

-continued

```
cagggtatgt ggatgcagcc aatccaccaa gcaacacaca caaaccgccc taccaccca      540 aaactggatg aaaatggtaa tccgattaca gaagatggta tttttgctca agctgattat      600
ggatattatg acgctcaaac ttatgccgaa ctgtctggca atgtcattat ggaacaaaac      660
ggtcggcgtg taaccgctga taagcttact ttagacaccc aaacagggca agccactgcg      720
tcaggtcaag tacaatttag tgatggcggt gcaagtgatc acagtgctgg cattattggc      780
atggctgaaa acttagtata ccatacagat ggtcagacag cgaccgcaca agatgttgct      840
tttgcaagca ctaccatcaa tgctcacggt tatgccagtc aaatggataa aataagcagt      900
agcgaatatc ggcttcaaca tgtcatgttc accacctgtc cacccacaga acgcaaatgg      960
tacttagata ctgatagcat tgatatcaat accgatacag gtcgtgctat cgccaaaaat     1020
accaccttgc gtatcaaaaa agtacctgtc ttttacctgc cctattttaa ctttccgatc     1080
gatgctcgtc gctcttctgg atttttatta ccatcaatgg gatttggtgc atcggacagt     1140
tttgaaatta gtacgcctta ttatctgaat ttggcaccag attatgatgc aaccattacg     1200
ccaactgtat ttactaaccg caatcctatg ctgactggcg aatttcgtta tctgacccaa     1260
gattatggat caggggtgtt gactgcttcg tatcttccaa aagatcagca atatcatgat     1320
aaagaccgta gccgaataca atttgatcat acatggcaac ccaagcagtt tgataaaatt     1380
accacttacg cacaatatca atctgtttct gatgccaatt atttatcaga ctttaatgcc     1440
ttgggtgttg agagtgctaa gctaaatcta ccaagacgca tcggcacaag cttcttggat     1500
gaaaatgtct cagctgattt aagatttgaa gattttcagc gtttagacgg ttttggctta     1560
gatggtcggc caattacaga caaagataga ccatatgcac gcctaccaca gctatcggtc     1620
aactatcgtt tgcctcgcat atggatgggt acacccagcg gtcttgaact gggtggtatt     1680
cataattctg cctatttcaa aaaatccatt aaagataact ctgaaccaga aaaaagcggt     1740
ggtagaatat ttaaccaatt cacagccagt tatccactgc ttcgctcttg gggttatttg     1800
acgccaaaac ttagcctgac acatctatat accagctatg acgaagacag cttagccgac     1860
caaaatatcg ctaagaaaaa tggtcgccat tcggtatttg caccgacggt cagcttggat     1920
gctgggctat ttttttgaaaaa agcgggtgca ccatttggca tgcatcaaga tacaggtggc     1980
tatcaagtac tgacaccaag attacactat acttacgcc ttttaaaga tcaacacaat      2040 gtaccaaatt ttgagacaaa aattgcacag cttagctatg agcagctttt gaacaataac      2100 tggttttttgg gtcatgatcg cattcaagat ttacacgccg tcacgcctgc agtcagctac      2160
cgttatatag ataaaatggg caggacacgc tttgaaggcg ggatcgcaga acagatttta      2220
ttgagtcata tccgtgttgg tatcaatgac agcgaaagct atagcagcag aagctctggt      2280
ttggcatggc aagccagcct acagccaaaa gacaatttat ggtttgatgc atcaggttca      2340
tttagaacaa attatgattt gagcagtatt gtggcacaaa ttcgctatcg tccaagtgat      2400
cgtaagttat taacctagg tattgtcaaa agaaagaaa atcgtgcttt taatcaatca      2460
gcattatcag catatactgc ctccgccatt tttccaatca ataatcgctg gcgtatgatg      2520
ggtcaactac aatacgacta caacttagat tatgtcatgg attctttgat ggggctaaat      2580
tatgaagatt gctgttatgg tttgtcaatc tatgcaagac gctatcgtga tgctttcaat      2640
ccacatttta caccctgatac tgcagtaatg gcagaagttc gcctaaacgg tatcggtggc      2700
ggcggtcgtt tgaatcgact tttgagcgaa aaggtactag gctatgatca ggttcgaaat      2760
gcttggagac atgattacta a                                                2781
```

<210> SEQ ID NO 2
<211> LENGTH: 926
<212> TYPE: PRT
<213> ORGANISM: Moraxella catarrhalis

<400> SEQUENCE: 2

```
Met His Thr Ala His His His Arg Ser Lys Thr Tyr Leu Thr Thr Ala
1               5                   10                  15

Ile Arg Tyr Ala Leu Phe Gly Ile Ala Ser Leu Pro Phe Val Ile Pro
            20                  25                  30

Thr Tyr Ala Glu Leu Asn Thr Ser Arg Ser Leu Thr Val Val Gly Ala
        35                  40                  45

Asp Ser Ser Lys Asn Leu Pro Asp Thr Pro Asn Thr Lys Pro Asn Thr
    50                  55                  60

Val Leu Ala Leu Asp Ala His Leu Gln Ser His Asp Asp Thr Ala Asn
65                  70                  75                  80

Ala Phe Asp Gly Phe Asp Phe Glu Val Ile Thr Gln Gln Ala Ala Glu
                85                  90                  95

Gln Thr Ser Ser Gln Ala Asn Gln Gly Asn His Gln Met Ser Gln Leu
            100                 105                 110

Asp Ala Phe Ala Ser Lys Ser Asp Asn Pro Ser Leu Asn Thr Ala Arg
        115                 120                 125

Leu Thr Asp Lys His Asp Thr Pro Ser Ala Ser Lys Ser Leu Ala Lys
    130                 135                 140

Leu Ala Glu Asn Tyr His Ile Lys Ser Asp Pro Asp Ala His Arg Cys
145                 150                 155                 160

Gln Gly Met Trp Met Gln Pro Ile His Gln Ala Thr His Thr Asn Arg
                165                 170                 175

Pro Thr Thr Pro Lys Leu Asp Glu Asn Gly Asn Pro Ile Thr Glu Asp
            180                 185                 190

Gly Ile Phe Ala Gln Ala Asp Tyr Gly Tyr Tyr Asp Ala Gln Thr Tyr
        195                 200                 205

Ala Glu Leu Ser Gly Asn Val Ile Met Glu Gln Asn Gly Arg Arg Val
    210                 215                 220

Thr Ala Asp Lys Leu Thr Leu Asp Thr Gln Thr Gly Gln Ala Thr Ala
225                 230                 235                 240

Ser Gly Gln Val Gln Phe Ser Asp Gly Gly Ala Ser Asp His Ser Ala
                245                 250                 255

Gly Ile Ile Gly Met Ala Glu Asn Leu Val Tyr His Thr Asp Gly Gln
            260                 265                 270

Thr Ala Thr Ala Gln Asp Val Ala Phe Ala Ser Thr Thr Ile Asn Ala
        275                 280                 285

His Gly Tyr Ala Ser Gln Met Asp Lys Ile Ser Ser Ser Glu Tyr Arg
    290                 295                 300

Leu Gln His Val Met Phe Thr Thr Cys Pro Pro Thr Glu Arg Lys Trp
305                 310                 315                 320

Tyr Leu Asp Thr Asp Ser Ile Asp Ile Asn Thr Asp Thr Gly Arg Ala
                325                 330                 335

Ile Ala Lys Asn Thr Thr Leu Arg Ile Lys Lys Val Pro Val Phe Tyr
            340                 345                 350

Leu Pro Tyr Phe Asn Phe Pro Ile Asp Ala Arg Arg Ser Ser Gly Phe
        355                 360                 365

Leu Leu Pro Ser Met Gly Phe Gly Ala Ser Asp Ser Phe Glu Ile Ser
    370                 375                 380
```

```
Thr Pro Tyr Tyr Leu Asn Leu Ala Pro Asp Tyr Asp Ala Thr Ile Thr
385                 390                 395                 400

Pro Thr Val Phe Thr Asn Arg Asn Pro Met Leu Thr Gly Glu Phe Arg
            405                 410                 415

Tyr Leu Thr Gln Asp Tyr Gly Ser Gly Val Leu Thr Ala Ser Tyr Leu
                420                 425                 430

Pro Lys Asp Gln Gln Tyr His Asp Lys Asp Arg Ser Arg Ile Gln Phe
        435                 440                 445

Asp His Thr Trp Gln Pro Lys Gln Phe Asp Lys Ile Thr Thr Tyr Ala
    450                 455                 460

Gln Tyr Gln Ser Val Ser Asp Ala Asn Tyr Leu Ser Asp Phe Asn Ala
465                 470                 475                 480

Leu Gly Val Glu Ser Ala Lys Leu Asn Leu Pro Arg Arg Ile Gly Thr
                485                 490                 495

Ser Phe Leu Asp Glu Asn Val Ser Ala Asp Leu Arg Phe Glu Asp Phe
                500                 505                 510

Gln Arg Leu Asp Gly Phe Gly Leu Asp Gly Arg Pro Ile Thr Asp Lys
        515                 520                 525

Asp Arg Pro Tyr Ala Arg Leu Pro Gln Leu Ser Val Asn Tyr Arg Leu
530                 535                 540

Pro Arg Ile Trp Met Gly Thr Pro Ser Gly Leu Glu Leu Gly Gly Ile
545                 550                 555                 560

His Asn Ser Ala Tyr Phe Lys Lys Ser Ile Lys Asp Asn Ser Glu Pro
                565                 570                 575

Glu Lys Ser Gly Gly Arg Ile Phe Asn Gln Phe Thr Ala Ser Tyr Pro
                580                 585                 590

Leu Leu Arg Ser Trp Gly Tyr Leu Thr Pro Lys Leu Ser Leu Thr His
        595                 600                 605

Leu Tyr Thr Ser Tyr Asp Glu Asp Ser Leu Ala Asp Gln Asn Ile Ala
    610                 615                 620

Lys Lys Asn Gly Arg His Ser Val Phe Ala Pro Thr Val Ser Leu Asp
625                 630                 635                 640

Ala Gly Leu Phe Phe Glu Lys Ala Gly Ala Pro Phe Gly Met His Gln
                645                 650                 655

Asp Thr Gly Gly Tyr Gln Val Leu Thr Pro Arg Leu His Tyr Thr Tyr
                660                 665                 670

Thr Pro Phe Lys Asp Gln His Asn Val Pro Asn Phe Glu Thr Lys Ile
            675                 680                 685

Ala Gln Leu Ser Tyr Glu Gln Leu Leu Asn Asn Trp Phe Leu Gly
    690                 695                 700

His Asp Arg Ile Gln Asp Leu His Ala Val Thr Pro Ala Val Ser Tyr
705                 710                 715                 720

Arg Tyr Ile Asp Lys Met Gly Arg Thr Arg Phe Glu Gly Gly Ile Ala
                725                 730                 735

Glu Gln Ile Leu Leu Ser His Ile Arg Val Gly Ile Asn Asp Ser Glu
                740                 745                 750

Ser Tyr Ser Ser Arg Ser Ser Gly Leu Ala Trp Gln Ala Ser Leu Gln
            755                 760                 765

Pro Lys Asp Asn Leu Trp Phe Asp Ala Ser Gly Ser Phe Arg Thr Asn
        770                 775                 780

Tyr Asp Leu Ser Ser Ile Val Ala Gln Ile Arg Tyr Arg Pro Ser Asp
785                 790                 795                 800

Arg Lys Leu Phe Asn Leu Gly Ile Val Lys Arg Lys Glu Asn Arg Ala
```

```
                  805                 810                 815
Phe Asn Gln Ser Ala Leu Ser Ala Tyr Thr Ala Ser Ala Ile Phe Pro
            820                 825                 830

Ile Asn Asn Arg Trp Arg Met Met Gly Gln Leu Gln Tyr Asp Tyr Asn
            835                 840                 845

Leu Asp Tyr Val Met Asp Ser Leu Met Gly Leu Asn Tyr Glu Asp Cys
            850                 855                 860

Cys Tyr Gly Leu Ser Ile Tyr Ala Arg Arg Tyr Arg Asp Ala Phe Asn
865                 870                 875                 880

Pro His Leu Ser Pro Asp Thr Ala Val Met Ala Glu Val Arg Leu Asn
            885                 890                 895

Gly Ile Gly Gly Gly Arg Leu Asn Arg Leu Leu Ser Glu Lys Val
            900                 905                 910

Leu Gly Tyr Asp Gln Val Arg Asn Ala Trp Arg His Asp Tyr
            915                 920                 925

<210> SEQ ID NO 3
<211> LENGTH: 957
<212> TYPE: DNA
<213> ORGANISM: Moraxella catarrhalis

<400> SEQUENCE: 3
gtgggtaaaa ttatgtcaaa aattcccatg atgaatgaaa agtattttcg tcgtcaggca      60
ctttattggt tgattgcggc ggctatcatg gcaggcttgt ggttgattgt ttggttgacc     120
agctccgtac cagcaatgat taataaacaa acgccaatc  aaacatcgtc ctatgttgcg     180
acattgccga ccacaatcac agcgttaaat gagcttgatc atgttgttaa gcccatggat     240
aattcggcac ttgtgcgaga cttacgcaac tatccacctg aatttaagga caaagtttat     300
tttaatggta ttagtggtcg ttataccatt gagctgatgg atgttaccga aaatgaagtt     360
atcgtggatt atctaaacag ccgagaagat cgtaacaatt ttgcttattt tcgctatact     420
gatgccaatg ataataagcg atatgtactg acttatggta aatttaccag tccagctgat     480
gcagaatctg ctttgcaaac cgtaaatttt agactgccaa atcagtgat  acaaaagacc     540 accaaaatct ctgagttggt cgcagtaatg gacaattatg aattgggtca gatgtggtg      600 gatttggcag acttccagcc tcgccgagtt cgcctgcaag cgacgcgtac cgaaattcca     660
gtcaaagcgg ccacgccagc agatgaagaa ttggcacgcc taagccgtga gcgtgcatta     720
caaacacaaa tttcccagca aactgagtcg gtcaggcagc cgactgattt ggatatccaa     780
aacgatatca atcgtttgtc taatcaaaga tctcaagtca gctctagcga tttgcctatg     840
gcaccaactg cacgcccaca gtcaccgcag caaacagccg atatagtacc caaaaatgaa     900
atatctaaag gcactgcacc aacccaaagc cattcggcag agacagaatc gcaataa       957

<210> SEQ ID NO 4
<211> LENGTH: 318
<212> TYPE: PRT
<213> ORGANISM: Moraxella catarrhalis

<400> SEQUENCE: 4

Val Gly Lys Ile Met Ser Lys Ile Pro Met Met Asn Glu Lys Tyr Phe
1               5                   10                  15

Arg Arg Gln Ala Leu Tyr Trp Leu Ile Ala Ala Ile Met Ala Gly
            20                  25                  30

Leu Trp Leu Ile Val Trp Leu Thr Ser Ser Val Pro Ala Met Ile Asn
            35                  40                  45
```

```
Lys Gln Asn Ala Asn Gln Thr Ser Ser Tyr Val Ala Thr Leu Pro Thr
    50                  55                  60

Thr Ile Thr Ala Leu Asn Glu Leu Asp His Val Val Lys Pro Met Asp
65                  70                  75                  80

Asn Ser Ala Leu Val Arg Asp Leu Arg Asn Tyr Pro Pro Glu Phe Lys
                85                  90                  95

Asp Lys Val Tyr Phe Asn Gly Ile Ser Gly Arg Tyr Thr Ile Glu Leu
                100                 105                 110

Met Asp Val Thr Glu Asn Glu Val Ile Val Asp Tyr Leu Asn Ser Arg
            115                 120                 125

Glu Asp Arg Asn Asn Phe Ala Tyr Phe Arg Tyr Thr Asp Ala Asn Asp
            130                 135                 140

Asn Lys Arg Tyr Val Leu Thr Tyr Gly Lys Phe Thr Ser Pro Ala Asp
145                 150                 155                 160

Ala Glu Ser Ala Leu Gln Thr Val Asn Phe Arg Leu Pro Lys Ser Val
                165                 170                 175

Ile Gln Lys Thr Thr Lys Ile Ser Glu Leu Val Ala Val Met Asp Asn
                180                 185                 190

Tyr Glu Leu Gly Gln Asp Val Val Asp Leu Ala Asp Phe Gln Pro Arg
            195                 200                 205

Arg Val Arg Leu Gln Ala Thr Arg Thr Glu Ile Pro Val Lys Ala Ala
            210                 215                 220

Thr Pro Ala Asp Glu Glu Leu Ala Arg Leu Ser Arg Glu Arg Ala Leu
225                 230                 235                 240

Gln Thr Gln Ile Ser Gln Gln Thr Glu Ser Val Arg Gln Pro Thr Asp
                245                 250                 255

Leu Asp Ile Gln Asn Asp Ile Asn Arg Leu Ser Asn Gln Arg Ser Gln
                260                 265                 270

Val Ser Ser Ser Asp Leu Pro Met Ala Pro Thr Ala Arg Pro Gln Ser
            275                 280                 285

Pro Gln Gln Thr Ala Asp Ile Val Pro Lys Asn Glu Ile Ser Lys Gly
            290                 295                 300

Thr Ala Pro Thr Gln Ser His Ser Ala Glu Thr Glu Ser Gln
305                 310                 315

<210> SEQ ID NO 5
<211> LENGTH: 35
<212> TYPE: DNA
<213> ORGANISM: Artificial
<220> FEATURE:
<223> OTHER INFORMATION: Primer

<400> SEQUENCE: 5
tatgtaccat ggctgaactc aataccagcc gttca                        35

<210> SEQ ID NO 6
<211> LENGTH: 36
<212> TYPE: DNA
<213> ORGANISM: Artificial
<220> FEATURE:
<223> OTHER INFORMATION: Primer

<400> SEQUENCE: 6
ggcatgctcg aggtaatcat gtctccaagc attttg                       36

<210> SEQ ID NO 7
<211> LENGTH: 31
```

```
<212> TYPE: DNA
<213> ORGANISM: Artificial
<220> FEATURE:
<223> OTHER INFORMATION: Primer

<400> SEQUENCE: 7
ggcagatctt ggaactcaat accagccgtt c                                      31

<210> SEQ ID NO 8
<211> LENGTH: 33
<212> TYPE: DNA
<213> ORGANISM: Artificial
<220> FEATURE:
<223> OTHER INFORMATION: Primer

<400> SEQUENCE: 8
acgcgtcgac ttagtaatca tgtctccaag cat                                    33

<210> SEQ ID NO 9
<211> LENGTH: 37
<212> TYPE: DNA
<213> ORGANISM: Artificial
<220> FEATURE:
<223> OTHER INFORMATION: Primer

<400> SEQUENCE: 9
cgtaccagca catatgaata aacaaaacgc caatcaa                                37

<210> SEQ ID NO 10
<211> LENGTH: 31
<212> TYPE: DNA
<213> ORGANISM: Artificial
<220> FEATURE:
<223> OTHER INFORMATION: Primer

<400> SEQUENCE: 10
gcccatctcg agttgcgatt ctgtctctgc c                                      31

<210> SEQ ID NO 11
<211> LENGTH: 33
<212> TYPE: DNA
<213> ORGANISM: Artificial
<220> FEATURE:
<223> OTHER INFORMATION: Primer

<400> SEQUENCE: 11
cgaggatcct aataaacaaa acgccaatca aac                                    33

<210> SEQ ID NO 12
<211> LENGTH: 31
<212> TYPE: DNA
<213> ORGANISM: Artificial
<220> FEATURE:
<223> OTHER INFORMATION: Primer

<400> SEQUENCE: 12
cagaagcttt tattgcgatt ctgtctctgc c                                      31

<210> SEQ ID NO 13
<211> LENGTH: 35
<212> TYPE: DNA
<213> ORGANISM: Artificial
<220> FEATURE:
<223> OTHER INFORMATION: Primer

<400> SEQUENCE: 13
```

```
tatgtaccat ggctgaactc aataccagcc gttca                                       35

<210> SEQ ID NO 14
<211> LENGTH: 36
<212> TYPE: DNA
<213> ORGANISM: Artificial
<220> FEATURE:
<223> OTHER INFORMATION: Primer

<400> SEQUENCE: 14
ggcatgctcg aggtaatcat gtctccaagc attttg                                      36
```